United States Patent
Fuesting et al.

(10) Patent No.: US 8,038,772 B2
(45) Date of Patent: Oct. 18, 2011

(54) FILTER CARTRIDGE FOR RECUPERATING HALOGENATED HYDROCARBONS

(75) Inventors: Bernd Fuesting, Berlin (DE); Peter Muenn, Berlin (DE); Hartmut Welke, Ahrensfelde (DE); Helmut Stach, Prieros (DE)

(73) Assignee: ZeoSys GmbH, Berlin (DE)

( * ) Notice: Subject to any disclaimer, the term of this patent is extended or adjusted under 35 U.S.C. 154(b) by 267 days.

(21) Appl. No.: 12/193,265

(22) Filed: Aug. 18, 2008

(65) Prior Publication Data
US 2009/0101010 A1    Apr. 23, 2009

Related U.S. Application Data

(63) Continuation of application No. PCT/EP2007/051520, filed on Feb. 16, 2007.

(30) Foreign Application Priority Data

Jul. 11, 2006 (EP) .................. 06117003

(51) Int. Cl.
*B01D 53/04* (2006.01)

(52) U.S. Cl. ............. 95/131; 95/903; 96/117.5; 96/132; 96/145; 96/147; 128/205.27

(58) Field of Classification Search .......... 95/131, 95/132, 143, 148, 903; 96/117.5, 131, 132, 96/134, 138, 151, 145, 147; 423/240 S; 128/205.12, 128/205.27
See application file for complete search history.

(56) References Cited

U.S. PATENT DOCUMENTS

| | | | |
|---|---|---|---|
| 3,375,933 A | 4/1968 | Rodman | |
| 3,592,191 A * | 7/1971 | Jackson | 128/203.28 |
| 3,680,283 A * | 8/1972 | Jones, Jr. | 96/138 |
| 3,941,573 A * | 3/1976 | Chapel | 96/135 |
| 4,559,066 A | 12/1985 | Hunter et al. | |
| 5,044,361 A | 9/1991 | Werner et al. | |
| 5,151,251 A | 9/1992 | Solcia et al. | |
| 5,515,845 A * | 5/1996 | Filipovic et al. | 128/205.12 |
| 6,306,290 B1 | 10/2001 | Rolfes | |
| 6,497,756 B1 | 12/2002 | Curado et al. | |

FOREIGN PATENT DOCUMENTS
EP    0 284 227 A2    9/1988

* cited by examiner

*Primary Examiner* — Frank Lawrence, Jr.
(74) *Attorney, Agent, or Firm* — Oblon, Spivak, McClelland, Maier & Neustadt, L.L.P.

(57) ABSTRACT

A filter cartridge for recovering halogenated hydrocarbons (HKW), such as those occurring in inhalation anesthetics in the medical field, contains a first gas inlet; a container which contains a filter insert; wherein the container is connected over a connection with a cover and with a gas release; wherein the container is united via two sealing rings and a filter plate with the cover; wherein the filter insert contains a zeolite; wherein the filter insert has openings; wherein the filter insert adapts with the base of the filter insert to recesses in the container.

21 Claims, 3 Drawing Sheets

FILTER CARTRIDGE FOR RECUPERATING HALOGENATED HYDROCARBONS

BACKGROUND OF THE INVENTION

1. Field of the Invention

The invention relates to a filter cartridge for recovery of low boiling point halogenated hydrocarbons, in particular, for recovering inhalation anesthetics from patient exhalent.

2. Discussion of the Background

Volatile anesthetic gases such as halothane, sevoflurane, enflurane, isoflurane and desflurane are frequently used in medical practice. These gases are chlorofluorocarbons (CFC) or hydrofluorocarbons (HFC). They will usually be entirely released into the environment during or after their use for anesthesia. This can be very harmful to patients and likely to medical personnel. In addition, such volatile anesthetic gases possess a potential to damage the environment, for example in the form of "ozone layer hole degradation" or "greenhouse effect". An estimation referring to the member states of the European Union showed that in 1995 alone, a load of the atmosphere of approximately 700 t arose from inhalation anesthetics. This quantity corresponds to 0.25% additional loading of the environment with carbon dioxide [Zeitschr. Anästhesiologie und Intensivmed. 6 (39), 301-306, 1998].

In the state of the art describing elimination of halogenated hydrocarbons from carrier gas, adsorption filters are used which function on the basis of micro-porous sorption material, such as activated charcoal and zeolites, for the purpose of temporary retention and storage of the gases. Reactive activated charcoal is already suitable for the cleaning of process of exhaust air (DE 37 13 346, DE 39 35 094 and DE 40 03 668). The conditions for a high sorption capacity of the sorption devices, connected with optimal regenerative power are already stated in the DD 239 947, DE 36 28 858 and DE 37 31 688. The recovery of halogenated hydrocarbons can take place economically with a high degree of recovery via desorption only under high temperatures and low pressures conditions. However, as a result of thermal treatment structural damages of the sorbent and also the formation of halogenated decomposition products of halogenated hydrocarbons arise.

In DE 37 13 346 and DE 195 49 271 the removing of halogenated hydrocarbons by means of zeolites is described. Zeolites are also particularly suitable for removing of pollutants from aqueous solutions (DE 44 06 766 and DE 195 31 933). The sorption of halogenated hydrocarbons is mentioned in DE 42 33 577. Recently, aluminum-poor and dealuminated zeolites have been used as sorbents (DE 195 32 500). Their alumina part (aluminium oxide) is substantially replaced by silicon dioxide. For example, dealumination of Na—Y-zeolites of the Wessalith DAY results in a favorable pore opening of 7.4 Å for the sorption of inhalation anesthetics. Zeolites exhibit a high thermal stability and a small catalytic activity for the formation of toxic products of halogenated hydrocarbons. The sorption of water to these so-called hydrophobic zeolites is noticeably reduced in favor of the sorption of halogenated hydrocarbons. A well-known procedure for the separation and recovery of inhalation anesthetics (DE 42 08 521) concerns their adsorption at activated charcoal or a zeolite filter with exception of the accompanying $N_2O$ (laughing gas), in which the remaining further carrier gases are afterwards supplied to a catalytic post combustion. The temperature of 550° C. that is required for this purpose is still uneconomically high. The recoverable active substances are irreversibly withdrawn from the device. A draw-back is that the narrow pores of the activated charcoal with a wide pore spectrum permanently adsorb halogenated hydrocarbons which can only be set free at high temperatures. Also, during the recovery of inhalation anesthetics (DE 43 08 940 and DE 195 49 271), the temperatures required for desorption in gas phase, 100° C. to 200° C., still lead to medically dangerous by-products.

One of the methods for recovering halogenated hydrocarbons from a gas stream (EP 0 284 227; CA 1 339 833) is using a hydrophobic zeolitic molecular sieve adsorbent with a narrow range pore distribution, which selectively separates the active substances of the group of halogenated ether from higher hydrocarbons. The desorption takes place in a container by means of a nitrogen purging gas stream at 30° C. to 150° C. The anesthetics are then condensed and recovered. However, a temperature range between 30° C. to 40° C. was not yet sufficient for an economically efficient degree of recovery. On the other hand, temperatures over approximately 140° C. lead to staining of the sorbent particles due to structural changes and development of coke deposition. Also, the spatial separation of the adsorption and the recovery cycles do not yet correspond to the economic requirements of a cycle of the exhalation gas.

In a method and device for the recovery of gases (DE 197 49 963; WO 99/22845), some anesthetics components are bound to the adsorbent, while others pass through it. In this method, dealuminated zeolites adapted to the process are already used favorably as sorbent material. Through thermal treatment, the adsorbed gas will be desorbed easily and condensed in a condenser and purified for reuse. Due to the high vapor pressure of the anesthetics, the condensation must take place within the temperature ranges of 2° C. to 8° C. The desorption of isoflurane takes place under vacuum (approx. 10 mbar) and under simultaneous heating at for instance 100° C. to 160° C. Thereby, the maximum desorption temperature is about 60° C. lower than that required for activated charcoal. Desflurane is desorbed between 90° C. and 130° C. Its low pressure, however, favors disadvantageously the deposit of coke-like materials due to the absence of oxidizable gas components.

In DE 101 18 768, a method is described concerning a gentle recovery of zeolites from a filter cartridge by a steam distillation of the sorbents. Modified and/or dealuminated zeolites with low water adsorption capacity below Ma-2% cause lowering of the desorption temperature which is favorable for the sorbents. Under normal pressure, a temperature limit is preferably 100° C. Additionally sorbed fractions of anesthetics are set free through the additional extraction. The dephlegmation of the rising gases leads to a partial condensation and to the return of the mixture into the evaporator with water as a main fraction. A further cooling of the gases leads to the development of a layer-like pre-separated mixture in a settling container. The specifically light-density water layer is recycled into the evaporation process, while the heavier-density layer from a post-purification is supplied for repeated use of the anesthetics. Other possible degradation products accumulate in the water layer. Thus, the developed harmful products remain in the water circulation and can be periodically removed.

Concerning adsorption and desorption of inhalation anesthetics, conventional filter cartridges with zeolites exhibit different characteristic parameters that depend substantially on flow and temperature conditions. In order to reach a standardization of the processing without a time delay, for example, a different energy supply from the outside into a cartridge is arranged, whereby the adsorbent anesthetics can be set free from the inside of the cartridge without time delay (EP 0 611 174, EP 1 222 940). Also, specially formed embodiments of filter cartridges for inhaled gases are usual in order to evenly use the fillings even at higher flow rates (DE 36 12 924) and to avoid local break-through of the adsorbents through the filter layer.

It is well-known from chemical engineering, that a cross-flow of gaseous phase and stationary sorbent is indicated when a sorptive is to be removed from the phase dispenser to a large extent. On the other hand, the loaded sorbent can be regenerated gradually with a changed regeneration fluid in the cross-flow cascade without a time delay.

Finally, domestic and commercial zeolites containing filter cartridges are neither suitable nor designed for a recovery of anesthetics by means of water vapor.

SUMMARY OF THE INVENTION

It is therefore an object of the present invention to solve the problems that are mentioned in the state of the art. It is another object to provide a filter cartridge suitable for the recovery of low boiling halogenated hydrocarbons, in particular from inhalation anesthetics.

This and other objects have been achieved by the present invention the first embodiment of which includes a filter cartridge, comprising:
a first gas inlet;
a container which comprises a filter insert;
wherein said container is connected over a connection with a cover and with a gas release;
wherein the container is united via two sealing rings and a filter plate with the cover;
wherein said filter insert contains a zeolite;
wherein the filter insert has openings;
wherein the filter insert adapts with the base of the filter insert to recesses in the container.

In another embodiment, the present invention provides a method for the recovery of a halogenated hydrocarbon, comprising:
contacting the filter cartridge as above with a carrier gas containing said halogenated hydrocarbon, to remove said halogenated hydrocarbon from said carrier gas and/or to temporarily store said halogenated hydrocarbon at an adsorption filter using modified and/or dealuminated zeolites; and
purposefully setting said halogenated hydrocarbon free if they have been temporarily stored at an adsorption filter.

DETAILED DESCRIPTION OF THE INVENTION

Figure 1:
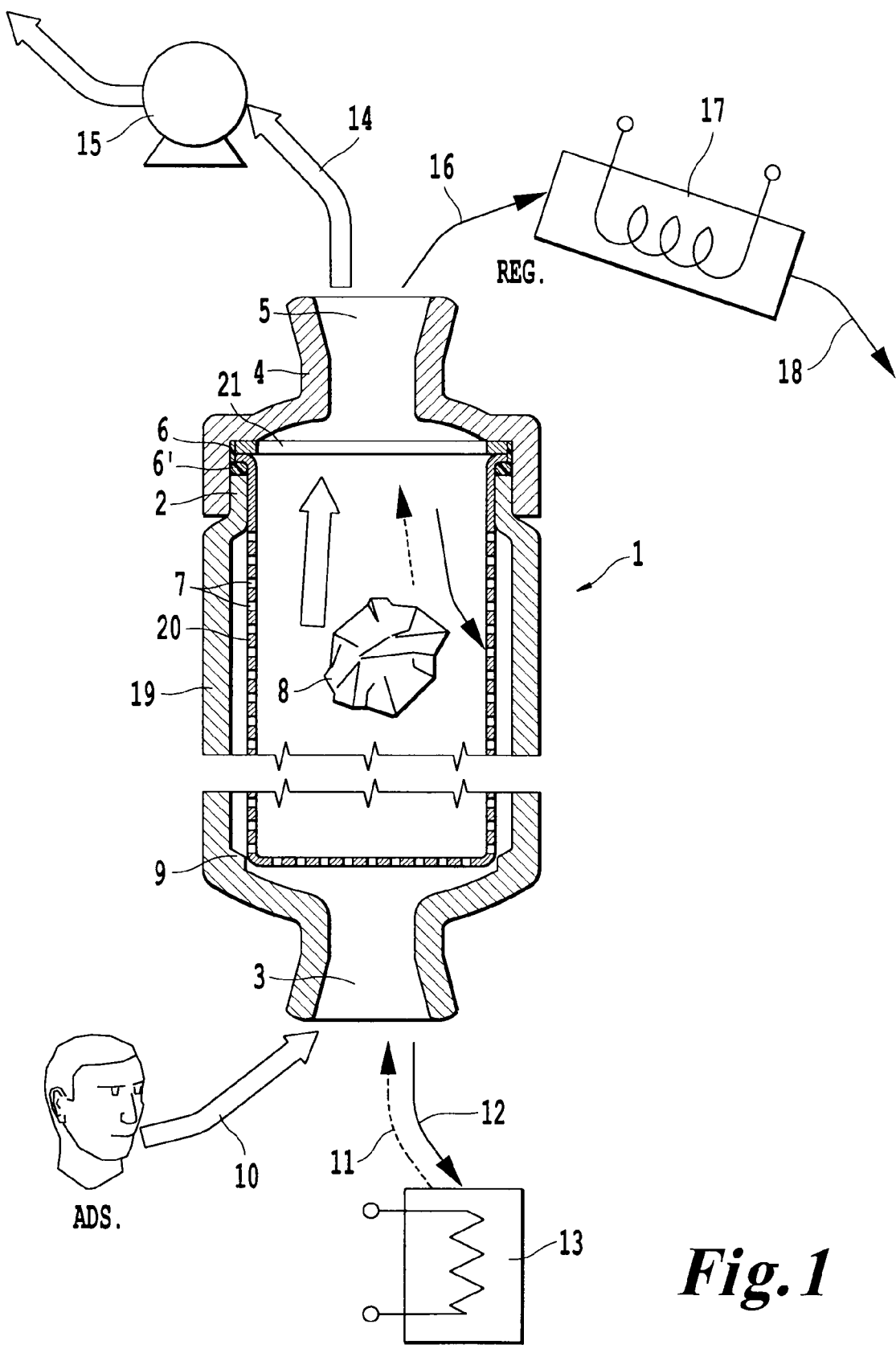
FIG. 1: Partial cross section of a filter cartridge for recovery of inhalation anesthetics in adsorption and regeneration processes.

The invention relates to a filter cartridge for recuperating low boiling point halogenated hydrocarbons (HKW), in particular, for inhalation anesthetics in the medical field. The aim of the invention is to develop a filter cartridge which enables simultaneous effective charging by adsorption and also useful regeneration by desorption by using vapor, outside of the anesthetic device without damaging hydrophobic zeolites and active carbons, in particular, molecular sieve carbons and the sorbate such as desflurane, isoflurane and sevoflurane.

In one embodiment, a filter cartridge for the recovery of halogenated hydrocarbons comprises a gas inlet (3) and is equipped with a container (19). The container (19) has a filter insert (20) and is connected over a connection (2) with a cover (4) and with a gas release (5). The container (19) is united via sealing rings (6; 6') and a filter plate (21) with the cover (4). A zeolite (8) is found in the filter insert (20) having openings (7). The filter insert (20) adapts with the base thereof to the recesses (9) in the container (19).

In a preferred embodiment of the invention, a sensor is found at the filter outlet so as to monitor the fill level.

Surprisingly, the present invention succeeded in developing a filter cartridge for both, effective loading by adsorption and an appropriate recovery through desorption using water vapor outside an anesthesia machine without possible damage to the sorbents and sorbat. A high spatial utilization rate is achieved for the sorbents. In one embodiment, this will be attained when the filter cartridge comprises to a large extent of a container with a cover around the filter insert and with the gas inlet for the exhalation gas, which is connected with a cover over the seal and this is further connected with the gas outlet. The seal is appropriately a screw connection or a bayonet connection. The filter cartridge has a filter insert with an upper ring with a filter plate for the attachment to the filter insert. The filter insert is placed between the top margin of the container and the cover by means of sealing rings and is jammed there. The zeolite in bulk form is found in the filter cartridge with its lateral openings in the wall and at the base. Between the inner wall of the container and the filter cartridge, an annular gap is present for the in-flowing inhalation gases as well as for the feedback of the regenerating water phase. In one embodiment, openings are intended in the filter cartridge for the gas and fluid inlet only in a larger and lower wall area of the container, while these are missing within the wall area of the cover or are locked by the wall of the container close to the upper sealing area. The filter cartridge exhibits a high slenderness ratio because the length of the lower range with the openings in the filter insert exceeds considerably the diameter of the insert as well as the length of the range with the missing openings. The flexible filter insert adapts with its lower base to the recesses in the container. Thereby, a flaring like lower tolerance gap is maintained at the same time. Water discharged from the filter insert can flow back with little hindrance. The cavities are brought into the base of the container in form of a strengthening fin. A fluid seal with a low height can be developed, which causes that the gases must first pass through the lowest layer of the sorbents and only then enter both, directly into the filter insert and the lateral annular gap between the filter insert and the container wall. The filter cartridge comprises an appropriate polymer material with strongly limited swellability when contacted with inhalation anesthetics.

The gas inlet is alternatively connected with a duct and a steam supply over plug connectors, stoppers and hoses. At the same time, the steam supply builds a reflux for the steam generator. The cover with the gas outlet leads on the one hand to exhaust gas duct as well as to a suction of exhaust air stream that is released from exhalation gas and on the other hand to a steam exhaust over a condenser into a collector for the condensed anesthetics. The gas inlet is likewise alternatively connected with the anesthesia machine or with steam generator over plug connector.

During the loading of the filter cartridge a multi-level adsorption of the exhalation gas in the cross flow takes place. Favorably, the loading of the sequential and still not exhausted stages takes place with same initial loading of exhalation gas. The loading with the gases drops gradually to the desired rest loading, whereby even small retention times are sufficient in order to achieve the demanded filter yield additionally with high gas or steam throughput. The gases pass thereby the bulk layer, which serve at the same time as droplet separator. The effectiveness of the filter cartridge is optimized for the purpose of high space utilization of the sorption-active filter part containing for example the zeolite. During the loading, the missing or locked gas passage openings in the upper wall region of the filter cartridge prevent the formation of a cross flow and produce within this region a plug flow of gas, whereby a standardization of the break-through curves for the anesthetics is obtained. In this way, the used anesthetic gases exhibit optimal break-through curves at the top margin of the filter insert with the hydrophobic zeolites. This means that a steep and clearly local as well as time determined characteristic of the transition is present in which a sharp border is formed between the loaded and still unloaded parts of the zeolite bulk.

Figure 4:
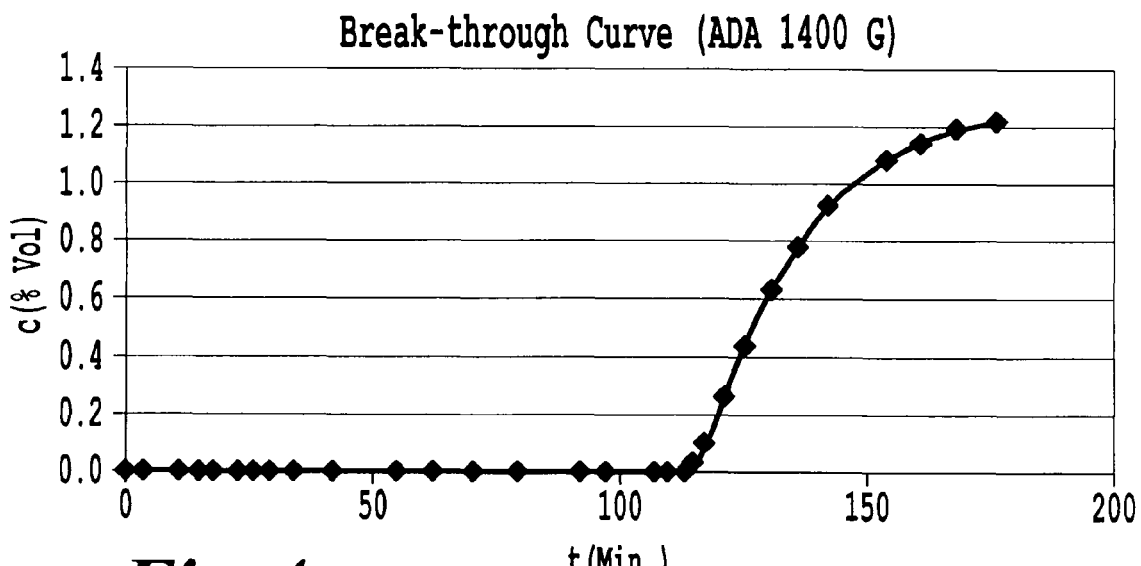
FIG. 4 shows a typical break-through curve.

A break-through curve generally shows the dependence of the anesthetic gas concentration on time. An example of a break-through curve is given in FIG. 4. At a time 0, the concentration is 0. However, it is to be understood that the present invention is not limited to a break-through curve as shown in FIG. 4.

The break-through region is the region in which the anesthetic gas concentration reaches a maximum level which depends on the application. Preferably, the concentration in the break-through region is in the order of not more than 3 vol. %.

It was further found that activated charcoal can be used in the filter, in particular hydrophobic molecular sieve coals with a water adsorption capacity below 2 Ma-%, whereby also the temperature for the desorption of the halogenated hydrocarbons is appropriately lowered. Moreover, combinations of zeolites and molecular sieve coals in form of a layer-wise sequence are preferably used. Preferably, at least one layer of a zeolite and at least one layer of a molecular sieve coal are used. The layer with lower sorption capacity is placed in proximity of the openings in the break-through region of the filter insert and the layer with higher sorption capacity is placed in the region of the gas inlet of the filter insert.

During the regeneration, water vapor rises in the annular gap between the container and the filter cartridge and penetrates into the openings of the bulk zeolite or bulk activated charcoal. Further rising vapors enter into the condenser. The bulk acts at the same time for the vapor as Dephlegmator, whereby the water turns back into the evaporator through the openings at the base and over the hollow in the tolerance gap outside of the filter insert. The backward-moving water is only partly discharged downward through the entire bulk. However, the larger part of the water is naturally being dripped in an inclined fashion toward the lowest edge zones of the filter insert under the force of gravity, whereby the water can be recycled without much hinderance through the openings in the annular gap and through the tolerance gap into the evaporator.

Appropriately, the height of the filter cartridge exceeds its diameter by at least around fourfold. The height of the break-through region is at least around eight times larger than the height of the filter insert. The internal diameter of the container is about 1.2-times larger than the outer diameter of the filter insert.

The optimal retention time of the anesthetic gases is determined by the gas exposure and the stream flow length of the filter insert. The speeds of the gases or vapors in the annular gap can be about 0.2 to 0.3 m/s, whereas the sprinkling strength during the regeneration reaches up to 0.4 $m^2/(m^2 h)$ without flooding taking place within the filter cartridge.

The openings in the filter insert that can be set up, are only insignificantly smaller than the size of the commercial formations of the zeolite particles, which are preferably supplied as hollow cylinder with main dimensions of 6/3 and/or 7/4 mm or as solid cylinder having main dimensions of 2 and/or 4 mm. Due to the size of the openings, favorable conditions are established for the fluid flow through the wall and the base region of the filter insert.

It is also possible to use commercially available sieves or knitted fabric with sufficient stability as filter inserts.

Modified and/or dealuminated zeolites with water adsorption capacity below Ma-2% are preferably used as sorbents, to lower the desorption temperature of halogenated hydrocarbons.

It is a particularly advantageous, that a commercially available domestic device can be attached to the filter cartridge as steam generator, e.g. steam cleaner or steam sterilizer, like those used in medical practice.

Since the adsorption isotherms of hydrophobic zeolites proceed in double-logarithmic stretching and rises quite flat as a function of the concentration or the pressure, the simple and well-known isotherms following Freundlich can be set to make estimations and further optimization of the filter cartridge [see T. Vermeulen, Separation by Adsorption Methods. Advances in Chem. Eng. 2 (1958), P. 147-203].

The method according to the invention for the recovery of halogenated hydrocarbons using the filter cartridge described above, comprises the recovery of halogenated hydrocarbons from carrier gases and/or temporarily storing in the adsorption filter by means of modified and/or dealuminated zeolites and purposefully releasing of the recovered halogenated hydrocarbons. Using a vapor carrier, the cooling of the vapor leads to the development of a phase related pre-separated mixture. The water layer having a low specific density is led back predominantly into the evaporation process of the water. The developed harmful products remain in a water circulation and are periodically or purposefully removed. A halogenated hydrocarbons layer having a high specific density can be recycled.

A high specific density is understood to be preferably in the order of 6.9-7.4 $g/cm^3$, without being limited to this exact range, while a low specific density is understood to be preferably in the order of not more than 1 $g/cm^3$, more preferably about 1 $g/cm^3$. Most preferably, a low specific density is in the order of >0 to about 1 $g/cm^3$.

Having generally described this invention, a further understanding can be obtained by reference to certain specific examples which are provided herein for purposes of illustration only, and are not intended to be limiting unless otherwise specified.

EXAMPLES

The associated FIGS. and the table show:

FIG. 1: Partial cross section of a filter cartridge for recovery of inhalation anesthetics in adsorption and regeneration processes.

Figure 2:
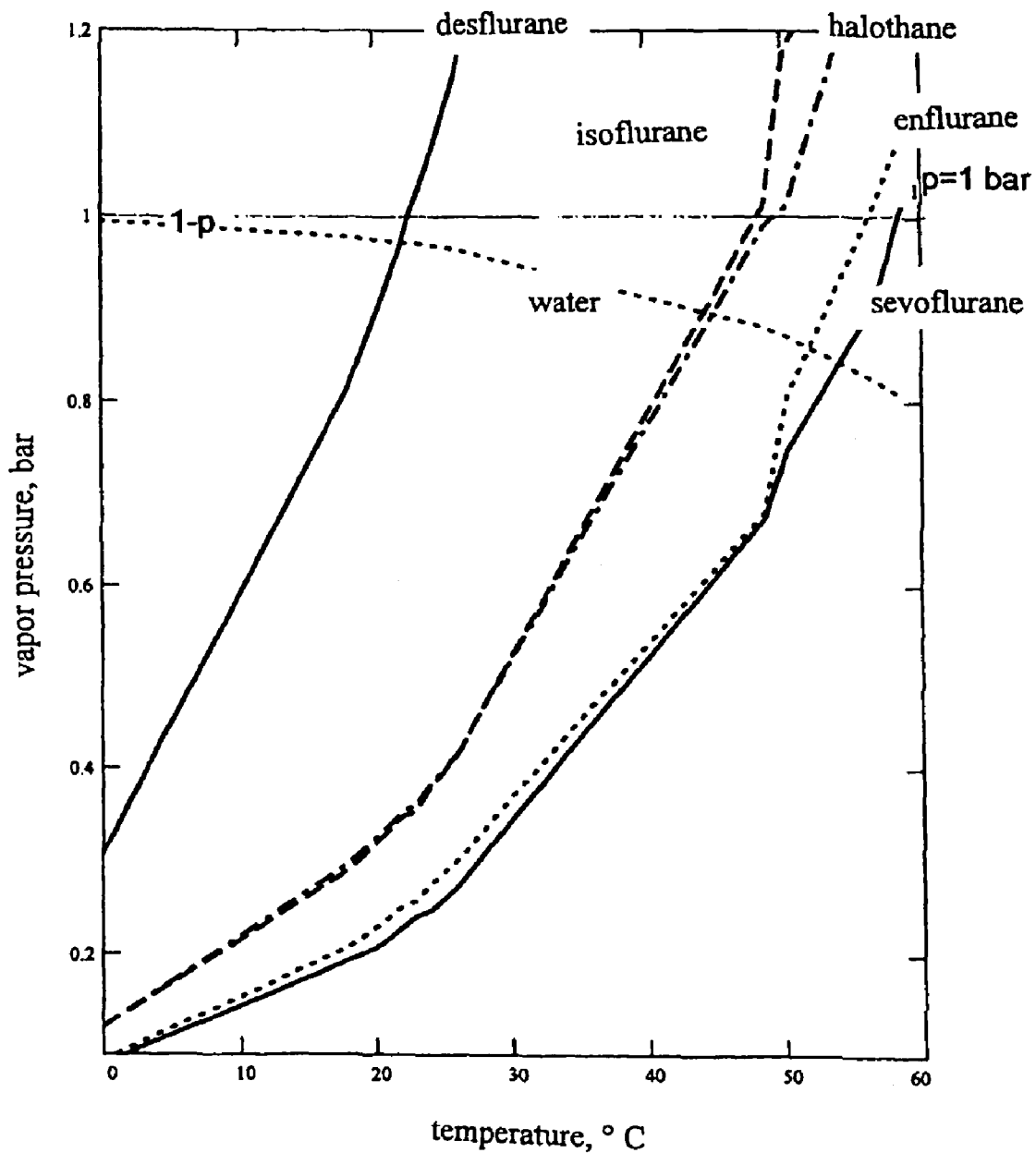
FIG. 2: Vapor pressure of water/anesthetics mixture as a function of temperature.

FIG. 2: Vapor pressure of water/anesthetics mixture as a function of temperature.

Figure 3:
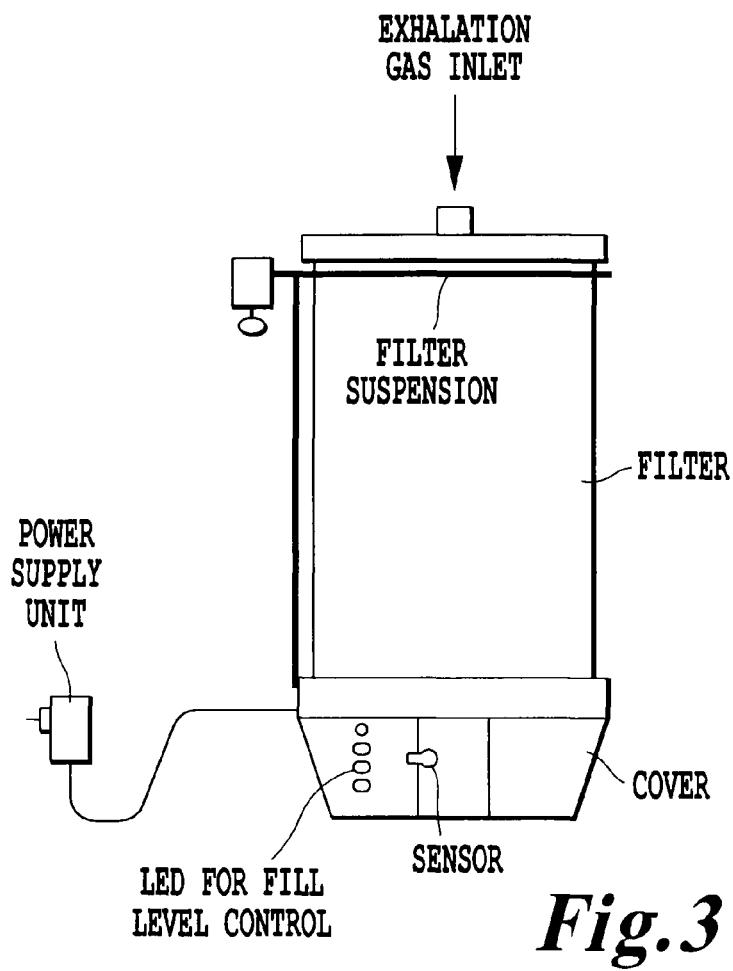
FIG. 3: Sensor at the filter exit for fill level monitoring.

FIG. 3: Sensor at the filter exit for fill level monitoring.

Tab. 1: Characteristics of inhalation anesthetics in correlation with water vapor.

REFERENCE SYMBOL LIST

| | |
|---|---|
| 1 | filter cartridge |
| 2 | connection |
| 3 | gas inlet |
| 4 | cover |
| 5 | gas outlet |
| 6, 6' | sealing rings |
| 7 | openings |
| 8 | zeolite |
| 9 | recesses |
| 10 | gas duct |
| 11 | steam supplier |
| 12 | reflux |
| 13 | steam generator |
| 14 | exhaust air discharge |
| 15 | suction |
| 16 | exhaust vapor duct |
| 17 | condenser |
| 18 | liquid discharge |
| 19 | container |

-continued

| | |
|---|---|
| 20 | filter insert |
| 21 | filter plate |

Dimensions of the filter insert (20) (not labeled):
H height of the filter insert (20)
h height of the breakdown region in the filter insert (20)
D diameters of the filter insert (20)

PREFERRED EXAMPLES

Example 1

The filter cartridge 1 according to FIG. 1 comprised a container 19 with gas outlet 5, which was united over a connection 2 with cover 4 and container 19 with gas inlet 3. The container 19 had a filter insert 20 that was connected by means of the sealing rings 6; 6' and a sieve plate 22 with cover 4. In filter insert 20 with openings 7 zeolite 8 was found. The filter insert 20 was adjusted with its base to recesses 9 in container 19.

The gas inlet 3 was optionally connected with a gas duct 10 and a steam supplier 11, which formed at the same time a reflux 12 and was connected with a steam generator 13. The cover 4 with gas outlet 5 lead on the one hand to an exhaust air discharge 14 and to an suction 15, on the other hand to an exhaust vapor duct 16 over a condenser 17 to a liquid discharge 18.

Example 2

The filter cartridge made an adsorption of inhalation anesthetics at already desorbed sorbents possible by optionally leading an exhalation flow gas through desorbed sorbents. According to Tab. 1 a lowering of the relative boiling point of the anesthetic and water mixture appeared at the limit range of 4 to 11%. The two components of the boiling mixture of inhalation anesthetics and water behaved over the entire concentration range, as if each was present alone. Their partial pressure in the vapor phase corresponds to the saturation pressure at the boiling temperature of the mixture, and the operating pressure selected here build up a normal pressure from the saturation pressure of the two components in accordance with FIG. 2. The almost absolute insolubility of liquid inhalation anesthetics in water favorably influenced the lowering of the boiling point. The sensitive anesthetics were preserved under thermal exposure. Their possible degradation products moved into the water phase through extraction.

TABLE 1

Characteristics of inhalation anesthetics in relation to water vapor

| Characteristics of inhalation anesthetics | sevoflurane | enflurane | isoflurane | haloethane | desflurane |
|---|---|---|---|---|---|
| Molecular weight [kg/kmol] | 200 | 184.5 | 184.5 | 197.5 | 168 |
| Specific gravity, g/cm³ (at 20° C.) | 1.53 | 1.52 | 1.5 | 1.86 | 1.47 |
| Relative density (Water = 1) | | 7.54 | 7.54 | 6.9 | 7.17 |
| Boiling point, ° C. at 1 bar | 58.6 | 56.5 | 48.6 | 50.2 | 22.8 |
| Boiling point decrease ° C., at a total pressure of 1 bar | 56.0 | 51.5 | 44.7 | 44.7 | 21.7 |
| Relative boiling point decrease [%] | 4.4 | 8.8 | 8.0 | 11.0 | 4.9 |

Example 3

A filter cartridge was filled with a micro-porous adsorbent (activated charcoal, hydrophobic zeolite) and served for recovery of volatile anesthetics from the exhalation gas of the patient. At filter exit, a fill level monitoring (semiconductor sensor for the detection of halogenated hydrocarbons) was mounted, with which the concentration of volatile anesthetics in the filtered exhaust air was determined. An electronic switching circuit operated the differently colored light emitting diodes (green, 2× yellow, red) as a function of the sensor values, so as to make an optical break-through control possible. The anesthetics were recovered from the returned loaded filters by means of desorption (FIG. 3).

Example 4

According to example 1, a filter cartridge with an empty mass of 0.77 kg was filled with about 0.6 kg zeolite (Tricat). With an exposure during a period of 3 days with a sevoflurane containing exhalation flow, a mass increase to 0.095 kg was observed, i.e. of 12%. The loaded zeolite was submitted in the filter cartridge in a distillation bridge over the steam generator. At the gas outlet, a descending type coil condenser was attached and the distillate was cooled at −0.5° C. into a receiving flask. With the occurrence of the first condensate drops a temperature of 57° C. was determined, which increased during the process (after a brief period with constant temperature) over approx. 20 min to 100° C. At the beginning, the liquid was cloudy but rapidly turned into clear liquid, which contained approximately ⅔ of the total obtained product with very little water. Two clear phases formed after a continuous distillation in the receiving flask. After approximately 45 minute, the receiving flask was filled to about 0.13l. About 0.06l or 0.089 kg of the distillate represents the heavy-density sevoflurane phase. The receiving flask is filled again during the next 30 minutes process, whereby predominantly water and only about 0.004 kg of sevoflurane were collected. The water vapor flow was a bit reduced, whereupon only 0.0012 kg of the final product was extracted. No further product was received in the next 60 minutes and the distillation was terminated. The total water condensate was about 0.4l. The weight related recovery degree of the sevoflurane resulted in about 95%.

Example 5

On filter cartridge 1, according to example 4, a commercial dephlegmator was placed with otherwise the same equipment. The recovery degree of the sevoflurane was increased to 97%.

Example 6

The filter insert 20 was filled with zeolites of different structure like Z-700, fine Z 700 and TZF, which had a sorption capacity of 0.21-0.26 kg/kg in relation to the sorbents. At a relatively short time (60-90 min) of the break-through of sevoflurane, a sharp profile of the break-through curves developed. The capacity of filter 1 was exploited, however this was set off by the shorter utilization periods.

Example 7

Molecular sieve coal was found in filter insert 20, which had a sorption capacity of 0.78 kg/kg of sorbents. A flat break-through curve occurred at relatively longer times (approx. 270 min) for the use of the filter cartridge 1. The filter efficiency was not entirely used despite its higher capacity.

Example 8

The three-fourth portion of the filter insert 20 was filled with a hydrophobic molecular sieve coal and a quarter with zeolites. The zeolite was placed above the coal. During the loading at filter cartridge 1 with sevoflurane, a favorable sharp break-through curve developed at extended utilization periods.

German patent application DE 10 2006 008 320.2 filed Feb. 17, 2006, and PCT/EP2007/051520, filed Feb. 16, 2007, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A filter cartridge, comprising:
a first gas inlet;
a container which comprises a filter insert;
wherein said container is connected over a connection with a cover and with a gas release;
wherein the container is united via two sealing rings and a filter plate with the cover;
wherein said filter insert contains a zeolite;
wherein the filter insert has openings;
wherein the filter insert adapts with the base of the filter insert to recesses in the container; and
wherein the gas inlet is connected with a gas duct and a steam supplier, which forms at the same time a reflux and is connected with a steam generator;
wherein the cover with the gas release leads on the one hand to an exhaust air discharge and to a suction, on the other hand to an exhaust vapor duct over a condenser to a liquid discharge.

2. The filter cartridge according to claim 1, wherein said two sealing rings serve as seals.

3. The filter cartridge according to claim 1, wherein a sensor is situated at the filter outlet for monitoring the fill level.

4. The filter cartridge according to claim 3, which is a semiconductor sensor.

5. The filter cartridge according to claim 3, wherein an electronic switching circuit operates differently colored light emitting diodes as a function of the sensor values, so as to make an optical break-through control possible;
wherein a green, two yellow, and one red light emitting diode are present.

6. The filter cartridge according to claim 1, wherein a height of the filter cartridge exceeds a diameter of said filter cartridge by at least a factor of four; and
wherein a height of a break-through region exceeds a height of the filter insert by at least a factor of eight.

7. The filter cartridge according to claim 1, wherein said openings in said filter insert are locked by the wall of the container.

8. A filter cartridge, comprising:
a first gas inlet;
a container which comprises a filter insert;
wherein said container is connected over a connection with a cover and with a gas release;
wherein the container is united via two sealing rings and a filter plate with the cover;
wherein said filter insert contains a zeolite;
wherein the filter insert has no openings in a break-through region;
wherein the filter insert adapts with the base of the filter insert to recesses in the container; and
wherein the gas inlet is connected with a gas duct and a steam supplier, which forms at the same time a reflux and is connected with a steam generator;
wherein the cover with the gas release leads on the one hand to an exhaust air discharge and to a suction, on the other hand to an exhaust vapor duct over a condenser to a liquid discharge.

9. The filter cartridge according to claim 1, comprising:
a) zeolites which are modified as sorbent formations and/or zeolites which dealuminated, said zeolites having a water adsorption capacity below 2 Ma-%;
or
b) activated charcoal having a water adsorption capacity below 2 Ma-%;
to decrease a desorption temperature of halogenated hydrocarbons which are placed in contact with said filter cartridge.

10. The filter cartridge according to claim 9, wherein said activated charcoal is a hydrophobic molecular sieve coal.

11. The filter cartridge according to claim 10, wherein a combination of zeolites and a molecular sieve coal are used in form of a layer sequence.

12. The filter cartridge according to claim 10, comprising at least one layer of zeolites and at least one layer of a molecular sieve coal.

13. The filter cartridge according to claim 12, wherein a layer with lower sorption capacity is arranged within a region of said openings of the filter insert, said openings being in a break-through region of the filter insert; and wherein a layer with higher sorption capacity is arranged within a region of said first gas inlet of said filter insert.

14. The filter cartridge according to claim 1, wherein each of said openings in the filter insert are only insignificantly smaller than the largest main dimension of the sorbent formations.

15. The filter cartridge according to claim 7, wherein the filter insert with said openings is a sieve or a knitted fabric.

16. The filter cartridge according to claim 1, wherein a speed of an exhalation gas in an annular gap between the container and the filter insert is 0.2-0.3 m/s and a sprinkling strength during a regeneration of said filter cartridge reaches up to 0.4 $m^3/(m^2h)$.

17. The filter cartridge according to claim 1, wherein an inside diameter of the container is about 1.2-times larger than an outside diameter of the filter insert.

18. A method for the recovery of a halogenated hydrocarbon, comprising:

contacting the filter cartridge according to claim 1 with a carrier gas containing said halogenated hydrocarbon, to remove said halogenated hydrocarbon from said carrier gas and/or to temporarily store said halogenated hydrocarbon at said filter insert using modified and/or dealuminated zeolites; and purposefully setting said halogenated hydrocarbon free if they have been temporarily stored at an adsorption filter.

19. The method according to claim 18, wherein said carrier gas is steam;

said method comprising developing a vapor;

cooling of the vapor which leads to the development of a phase related pre-separated mixture;

a water layer having a low specific density is led back predominantly into an evaporation process of the water;

developed harmful products remain in a water circulation, periodically or purposefully to be removed so as to make use repetitive of the specifically heavy-density halogenated hydrocarbons layer.

20. The method according to claim 18, wherein a speed of an exhalation gas in an annular gap between the container and the filter insert is 0.2-0.3 m/s and a sprinkling strength during a regeneration of said filter cartridge reaches up to 0.4 $m^3/(m^2h)$.

21. The method according to claim 18, wherein said halogenated hydrocarbon is contained in an inhalation anesthetic.

* * * * *